United States Patent [19]

Bundy

[11] 4,144,273
[45] Mar. 13, 1979

[54] 2-DECARBOXY-2-ALKYLCARBONYL-3,7-INTER-M-PHENYLENE-3-OXA-4,5,6-TRI-NOR-11-DEOXY-PGF$_1$ COMPOUNDS

[75] Inventor: Gordon L. Bundy, Portage, Mich.

[73] Assignee: The Upjohn Company, Kalamazoo, Mich.

[21] Appl. No.: 925,263

[22] Filed: Jul. 17, 1978

Related U.S. Application Data

[62] Division of Ser. No. 888,695, Mar. 21, 1978, Pat. No. 4,123,463.

[51] Int. Cl.$^2$ .......................................... C07C 177/00
[52] U.S. Cl. .................................................. 260/590 C
[58] Field of Search ...................................... 260/590 C

[56] References Cited

U.S. PATENT DOCUMENTS

| | | | |
|---|---|---|---|
| 3,931,296 | 1/1976 | Hayashi et al. | 260/514 D |
| 3,953,435 | 4/1976 | Hayashi et al. | 260/240 R |
| 4,066,751 | 1/1978 | Hayashi et al. | 424/180 |

OTHER PUBLICATIONS

Derwent, Farmdoc CPF, No. 93049x

Primary Examiner—Gerald A. Schwartz
Attorney, Agent, or Firm—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

33 Claims, No Drawings

2-DECARBOXY-2-ALKYLCARBONYL-3,7-INTER-M-PHENYLENE-3-OXA-4,5,6-TRINOR-11-DEOXY-PGF$_1$ COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from U.S. Pat. No. 4,123,463.

I claim:

1. A prostaglandin analog of the formula

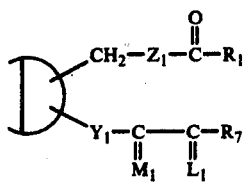

wherein 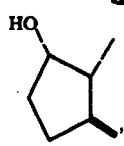 is

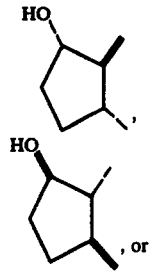

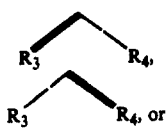

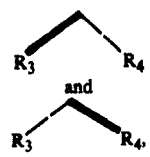

wherein $R_1$ is alkyl of one to 4 carbon atoms, inclusive;
wherein $L_1$ is

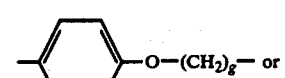

a mixture of

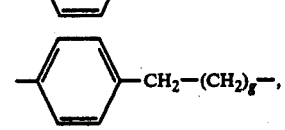

wherein $R_3$ and $R_4$ are hydrogen, methyl, or fluoro, being the same or different, with the proviso that one of $R_3$ and $R_4$ is methyl only when the other is hydrogen or methyl;

wherein $M_1$ is

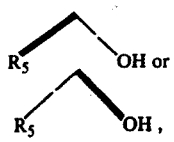

wherein $R_5$ is hydrogen or methyl;
wherein $R_7$ is (1) —(CH$_2$)$_m$—CH$_3$,

(2)

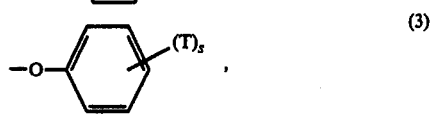

(3)

wherein h is zero to three, inclusive,
wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;

wherein $Y_1$ is
(1) trans—CH=CH—
(2) cis—CH=CH—
(3) —CH$_2$CH$_2$—, or
(4) —C≡C—; and wherein $Z_1$ is (1)

(2)

wherein g is one, two or three.

2. A prostaglandin analog according to claim 1, wherein $R_1$ is methyl.

3. A prostaglandin analog according to claim 2, wherein D is

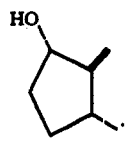

4. 2-Decarboxy-2-methylcarbonyl-3,7-inter-m-phenylene-3-oxa-4,5,6-trinor-11-deoxy-8β,12α-PGF$_2$α, a prostaglandin analog according to claim 3.

5. A prostaglandin analog according to claim 2, wherein D is

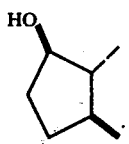

6. 2-Decarboxy-2-methylcarbonyl-3,7-inter-m-phenylene-3-oxa-4,5,6-trinor-11-deoxy-PGF$_2\beta$, a prostaglandin analog according to claim 5.

7. A prostaglandin analog according to claim 2, wherein D is

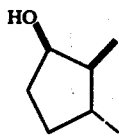

8. 2-Decarboxy-2-methylcarbonyl-3,7-inter-m-phenylene-3-oxa-4,5,6-trinor-11-deoxy-8$\beta$,12$\alpha$-PGF$_2\beta$, a prostaglandin analog according to claim 7.

9. A prostaglandin analog accoridng to claim 2, wherein D is

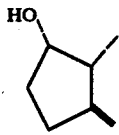

10. A prostaglandin analog according to claim 9, wherein Y$_1$ is cis—CH=CH—.

11. 2-Decarboxy-2-methylcarbonyl-3,7-inter-m-phenylene-3-oxa-4,5,6-trinor-13-cis-11-deoxy-PGF$_1\alpha$, a prostaglandin analog according to claim 10.

12. A prostaglandin analog according to claim 9, wherein Y$_1$ is —CH$_2$CH$_2$—.

13. 2-Decarboxy-2-methylcarbonyl-3,7-inter-m-phenylene-3-oxa-4,5,6-trinor-13,14-dihydro-11-deoxy-PGF$_1\alpha$, a prostaglandin analog according to claim 12.

14. A prostaglandin analog according to claim 9, wherein Y$_1$ is —C≡C—.

15. 2-Decarboxy-2-methylcarbonyl-3,7-inter-m-phenylene-3-oxa-4,5,6-trinor-13,14-didehydro-11-deoxy-PGF$_1\alpha$, a prostaglandin analog according to claim 14.

16. A prostaglandin analog according to claim 9, wherein Y$_1$ is trans—CH=CH—.

17. A prostaglandin analog according to claim 16, wherein R$_7$ is

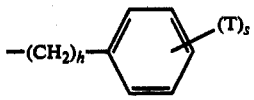

18. 2-Decarboxy-2-methylcarbonyl-3,7-inter-m-phenylene-3-oxa-4,5,6-18,19,20-hexanor-17-phenyl-11-deoxy-PGF$_1\alpha$, a prostaglandin analog according to claim 17.

19. A prostaglandin analog according to claim 16, wherein R$_7$ is

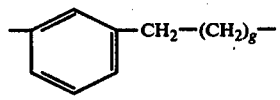

20. 2-Decarboxy-2-methylcarbonyl-3,7-inter-m-phenylene-3-oxa-4,5,6-17,18,19,20-heptanor-16-phenoxy-11-deoxy-PGF$_1$60, a prostaglandin analog according to claim 19.

21. A prostaglandin analog according to claim 19, wherein R$_7$ is (CH$_2$)$_m$—CH$_3$—.

22. A prostaglandin analog according to claim 21, wherein Z$_1$ is

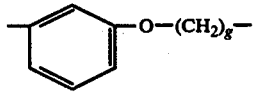

23. 2-Decarboxy-2-methylcarbonyl-3,7-inter-m-phenylene-4,5,6-trinor-11-deoxy-PGF$_1\alpha$, a prostaglandin analog according to claim 22.

24. A prostaglandin analog according to claim 21, wherein Z$_1$ is

25. A prostaglandin analog according to claim 21, wherein R$_5$ is methyl.

26. 2-Decarboxy-2-methylcarbonyl-3,7-inter-m-phenylene-3-oxa-4,5,6-trinor-15-methyl-11-deoxy-PGF$_1\alpha$, a prostaglandin analog according to claim 21.

27. A prostaglandin analog according to claim 21, wherein R$_5$ is hydrogen.

28. A prostaglandin analog according to claim 27, wherein one of R$_3$ and R$_4$ is fluoro.

29. 2-Decarboxy-2-methylcarbonyl-3,7-inter-m-phenylene-3-oxa-4,5,6-trinor-16,16-difluoro-11-deoxy-PGF$_1\alpha$, a prostaglandin analog according to claim 28.

30. A prostaglandin analog according to claim 27, wherein at least one of R$_3$ and R$_4$ is methyl.

31. 2-Decarboxy-2-methylcarbonyl-3,7-inter-m-phenylene-3-oxa-4,5,6-trinor-16,16-dimethyl-11-deoxy-PGF$_1\alpha$, a prostaglandin analog according to claim 30.

32. A prostaglandin analog according to claim 27, wherein R$_3$ and R$_4$ are both hydrogen.

33. 2-Decarboxy-2-methylcarbonyl-3,7-inter-m-phenylene-3-oxa-4,5,6-trinor-11-deoxy-PGF$_1\alpha$, a prostaglandin analog according to claim 32.

* * * * *

UNITED STATES PATENT OFFICE
CERTIFICATE OF CORRECTION

Patent No. 4,144,273　　　　　　　　　　Dated　March 13, 1979

Inventor(s)　Gordon L. Bundy

It is certified that error appears in the above-identified patent and that said Letters Patent are hereby corrected as shown below:

Column 2, lines 39-48,

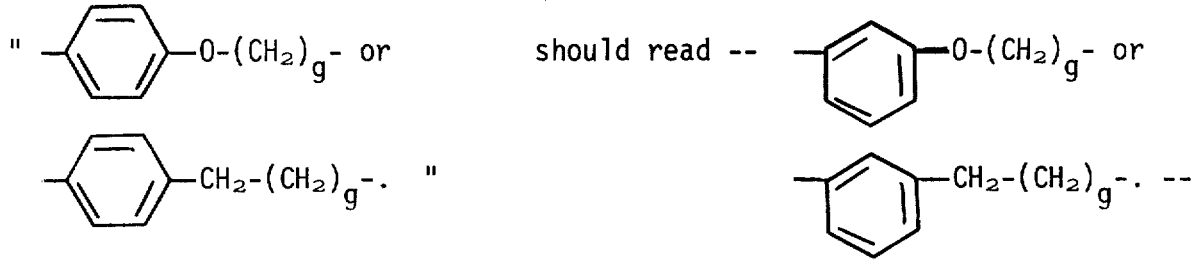

Column 2, line 65, "$PGF_{2\alpha}$" should read -- $PGF_{1\alpha}$ --;
Column 3, line 9 and 22, "$PGF_{2\beta}$" should read -- $PGF_{1\beta}$ --; line 49, "-CH≡CH-." should read -- -CH=CH-. --;
Column 4, line 13, "$PGF_{160}$" should read -- $PGF_{1\alpha}$ --; line 15, "claim 19" should read -- claim 21 --; line 16, "$(CH_2)_m$-$CH_3$-" should read -- $(CH_2)_m$-$CH_3$ --.

Signed and Sealed this

Seventh Day of August 1979

[SEAL]

Attest:

LUTRELLE F. PARKER
Attesting Officer　　　　　Acting Commissioner of Patents and Trademarks